(12) United States Patent
Zeng et al.

(10) Patent No.: US 10,766,851 B1
(45) Date of Patent: Sep. 8, 2020

(54) METHOD TO CONVERT LIGNIN 4-O-5 DIARYL ETHERS AND THEIR MODEL COMPOUNDS INTO ORGANIC CHEMICALS

(71) Applicants: LANZHOU UNIVERSITY, Lanzhou Shi (CN); THE ROYAL INSTITUTION FOR THE ADVANCEMENT OF LEARNING / MCGILL UNIVERSITY, Montréal (CA)

(72) Inventors: Huiying Zeng, Lanzhou (CN); Chao-Jun Li, Brossard (CA); Dawei Cao, Wuwei (CN)

(73) Assignee: THE ROYAL INSTITUTION FOR THE ADVANCEMENT OF LEARNING / MCGILL UNIVERSITY, Montréal (CA)

( * ) Notice: Subject to any disclaimer, the term of this patent is extended or adjusted under 35 U.S.C. 154(b) by 0 days.

(21) Appl. No.: 16/547,748

(22) Filed: Aug. 22, 2019

(51) Int. Cl.
*C07C 209/18* (2006.01)
*B01J 23/44* (2006.01)

(52) U.S. Cl.
CPC ............. *C07C 209/18* (2013.01); *B01J 23/44* (2013.01)

(58) Field of Classification Search
CPC ............................... C07C 209/18; B01J 23/44
USPC ........................................................... 564/399
See application file for complete search history.

(56) References Cited

PUBLICATIONS

Zeng et al., Angewandte Chemie International Edition, (2018), 57(14), p. 3752-3757.*
Zeng et al., Angewandte Chemie International Edition, (2018), 57(14), p. 3752-3757, supporting information S1-S64.*

* cited by examiner

*Primary Examiner* — Yong L Chu
(74) *Attorney, Agent, or Firm* — Norton Rose Fulbright

(57) ABSTRACT

It is provided a method of converting a diaryl ether source such as lignin and/or polyphenylene oxide (PPO) containing 4-O-5 linkages and an inorganic chemical such as ammonia into an organic compound, comprising reacting said diaryl ether source with the inorganic chemical in presence of a catalyst, preferably palladium, transforming the 4-O-5 linkages of said diaryl ether source into the organic compound. It is provided a palladium-catalyzed synthesis of aniline derivatives from 4-O-5 linkage lignin model compounds and cheap industrial inorganic chemical ammonia via dual C(Ar)—O bond cleavage.

15 Claims, 2 Drawing Sheets

METHOD TO CONVERT LIGNIN 4-O-5 DIARYL ETHERS AND THEIR MODEL COMPOUNDS INTO ORGANIC CHEMICALS

TECHNICAL FIELD

It is provided a method of converting a diaryl ether source such as lignin and/or polyphenylene oxide (PPO) into organic recycled compounds.

BACKGROUND

Converting lower value renewable biomass, e.g., forestry and agricultural wastes, and disused polymers such as polyphenylene oxide (PPO) into higher value-added chemical products is becoming increasingly important for social, economic, and resource sustainability. Lignin is a major renewable biomass waste product in the pulp and paper industry, with a production of 150-180 million tons per year. On the other hand, polyphenylene oxide (PPO) is widely used as important engineering-plastics. Diaryl ether, a common 4-O-5 linkage lignin model compound and the building block of PPO, has the highest bond dissociation energy among the three types of ether linkages (including α-O-4, β-O-4 and 4-O-5) in lignins, and is the most challenging to cleave. Thus far, success has been achieved to cleave this type of ether bond to form simple molecules, including hydrocarbon (benzene, cyclohexane) and oxygen-containing compounds (phenol, cyclohexanol, cyclohexanone, and cyclohexylalkyl ether).

Converting cheap inorganic chemicals into high value-added organic chemicals has very important economic value.

There is thus still a need to be provided with means to convert lower value renewable biomass into high value-added organic chemicals.

SUMMARY

It is provided a method of converting a diaryl ether source containing 4-O-5 linkages and an inorganic chemical into organic compounds, comprising reacting said diaryl ether source with the inorganic chemical in presence of a catalyst, transforming the 4-O-5 linkages of said diaryl ether source into the organic compounds.

In an embodiment, the diaryl ether source is lignin, polyphenylene oxide (PPO), or a substituted diaryl ether.

In a further embodiment, the R1 and R2 are the same or different substituents on the arenes.

In another embodiment, the substituents are hydrogen, alkyl, halogen, alkoxyl, arylxy, ester, hydroxyl, amine, nitro, aryl or acyl groups.

In an additional embodiment, the inorganic chemical is urea, ammonium bicarbonate, ammonium chloride, hydrazine hydrate, ammonium hydroxide or ammonia gas.

In a particular embodiment, the catalyst is palladium.

In an embodiment, the catalyst is $Pd(OH)_2/C$.

In another embodiment, the organic compound is at least one of an aniline derivative and an arene.

In a further embodiment, the method provided herein further comprises reacting said diaryl ether source, the inorganic chemical and the catalyst with a reducing agent.

In another embodiment, the reducing agent is $HCO_2Na$, formic acid, ammonium formate, NaH, $H_2$ or $NaBH_4$.

In an embodiment, the method provided herein further comprises reacting said diaryl ether source, the inorganic chemical and the catalyst with a solvent.

In an embodiment, the solvent is m-xylene, o-xylene, p-xylene, toluene or 1,4-dioxane.

In a further embodiment, the diaryl ether source is reacted with 5 equiv of ammonium hydroxide.

In another embodiment, the reducing agent is 1 equiv of $NaBH_4$.

In a further embodiment, the diaryl ether source, the inorganic chemical and the catalyst are contacted at a temperature between 140° C. to 160° C.

In an embodiment, the diaryl ether source and the inorganic chemical are contacted with 10 mol % to 30 mol % of the catalyst.

In a further embodiment, the said diaryl ether source, the inorganic chemical and the catalyst are reacted for 12 to 36 h.

BRIEF DESCRIPTION OF THE DRAWINGS

Reference will now be made to the accompanying drawings.

DETAILED DESCRIPTION

It is provided a method of converting a diaryl ether source such as lignin and/or polyphenylene oxide (PPO) containing 4-O-5 linkages and an inorganic chemical such as ammonia into an organic compound, comprising reacting said diaryl ether source with the inorganic chemical in presence of a catalyst, preferably palladium, transforming the 4-O-5 linkages of said diaryl ether source into the organic compounds.

Accordingly, it is described a palladium-catalyzed synthesis of aniline derivatives from 4-O-5 linkage lignin model compounds and cheap industrial inorganic chemical ammonia via dual C(Ar)—O bond cleavage.

The conversion of renewable resources and cheap inorganic chemicals directly into higher value-added organic chemicals is becoming more and more important for future sustainable development. Lignin, being the second most abundant organic carbon renewable resource on Earth, has been treated as waste in the pulp and paper industry. The 4-O-5 linkage diaryl ether bond, is the strongest among the three types of ether linkages in lignins.

Ammonia is a very inexpensive industrial inorganic chemical. Herein, it is reported a direct conversion of diaryl ethers and ammonia into aniline derivatives and arenes, providing a model for selective lignin 4-O-5 linkage modification and PPO recycling with cheap ammonia. Both symmetrical and unsymmetrical diaryl ethers were successfully cross-coupled with ammonia via dual C(Ar)—O bond cleavages, generating the corresponding cyclohexylanilines and arenes.

Towards the valorization of lignin and PPO waste into higher value-added chemicals, it is provided a new method of reacting diaryl ethers with organic amines to form nitrogen-containing compounds.

Figure 1:
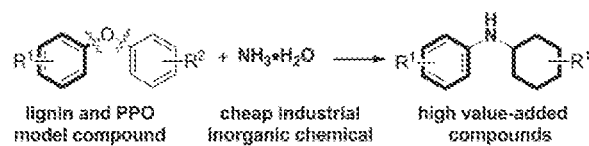
FIG. 1 illustrates strategies for converting 4-O-5 linkage lignin or PPO model compounds and ammonia into high value-added anilines, showing transformation of 4-O-5 linkage lignin or PPO model diaryl ethers with ammonia into aniline derivatives, catalyzed by palladium in accordance to another embodiment.

Ammonia is a very cheap and abundant industrial inorganic chemical. Converting lignin or PPO waste with ammonia directly into high value-added nitrogen-containing organic chemicals provides a great economic advantage for lignin utilizations and PPO recycling. At the same time, anilines are important building blocks for various organic molecules and electronic materials, as well as among the most prevalent structural motifs among pharmaceutical agents. Thus, methods that can directly react lignin or PPO waste with ammonia to produce higher valued products were explored and herein, it is reported the direct transformation of 4-O-5 linkage lignin or PPO model diaryl ethers with ammonia into aniline derivatives, catalyzed by palladium (FIG. 1).

Firstly, different palladium catalysts were screened to couple diphenyl ether with ammonium chloride (Table 1, entries 1-4).

TABLE 1

Evaluation of various conditions[a]

| Entry | Catalyst | 2a | Solvent | [H] | 3a[b]/% | 4a[b]/% |
|---|---|---|---|---|---|---|
| 1 | Pd(OH)$_2$/C | NH$_4$Cl | toluene | HCO$_2$Na | 2 | n.p. |
| 2 | Pd/C | NH$_4$Cl | toluene | HCO$_2$Na | trace | n.p |
| 3 | Pd/Al$_2$O$_3$ | NH$_4$Cl | toluene | HCO$_2$Na | n.p. | n.p, |
| 4 | Pd(OAc)$_2$ | NH$_4$Cl | toluene | HCO$_2$Na | n.p. | n.p. |
| 5 | Pd(OH)$_2$/C | NH$_4$Cl | m-xylene | HCO$_2$Na | 6 | n.p. |
| 6 | Pd(OH)$_2$/C | NH$_4$Cl | 1,4-dioxane | HCO$_2$Na | n.p. | n.p. |
| 7 | Pd(OH)$_2$/C | urea | m-xylene | HCO$_2$Na | 16 | n.p. |
| 8 | Pd(OH)$_2$/C | NH$_4$HCO$_3$ | m-xylene | HCO$_2$Na | 26 | n.p. |
| 9 | Pd(OH)$_2$/C | NH$_3$ · H$_2$O | m-xylene | HCO$_2$Na | 30 | n.p. |
| 10 | Pd(OH)$_2$/C | N$_2$H$_4$ · H$_2$O | m-xylene | HCO$_2$Na | 12 | n.p. |
| 11 | Pd(OH)$_2$/C | NH$_3$ | m-xylene | HCO$_2$Na | 8 | n.p. |
| 12[c] | Pd(OH)$_2$/C | NH$_3$ · H$_2$O | m-xylene | HCO$_2$Na | 9 | n.p. |
| 13[d] | Pd(OH)$_2$/C | NH$_3$ · H$_2$O | m-xylene | HCO$_2$Na | 43 | n.p. |
| 14[e] | Pd(OH)$_2$/C | NH$_3$ · H$_2$O | m-xylene | HCO$_2$Na | 35 | n.p. |
| 15[d] | Pd(OH)$_2$/C | NH$_3$ · H$_2$O | m-xylene | NaBH$_4$ | 49 | 2 |
| 16[d] | Pd(OH)$_2$/C | NH$_3$ · H$_2$O | m-xylene | NaH | 25 | n.p. |
| 17[d,f] | Pd(OH)$_2$/C | NH$_3$ · H$_2$O | m-xylene | NaBH$_4$ | 72 | 2 |
| 18[d,g] | Pd(OH)$_2$/C | NH$_3$ · H$_2$O | m-xylene | NaBH$_4$ | 79 | 3 |
| 19[d,h] | Pd(OH)$_2$/C | NH$_3$ · H$_2$O | m-xylene | NaBH$_4$ | 48 | 2 |
| 20[d,g,i] | Pd(OH)$_2$/C | NH$_3$ · H$_2$O | m-xylene | NaBH$_4$ | 87(83) | 5 |
| 21[d,g,j] | Pd(OH)$_2$/C | NH$_3$ · H$_2$O | m-xylene | NaBH$_4$ | 69 | 3 |
| 22[d,g,i,k] | Pd(OH)$_2$/C | NH$_3$ · H$_2$O | m-xylene | NaBH$_4$ | 64 | 5 |
| 23[d,g,i,m] | Pd(OH)$_2$/C | NH$_3$ · H$_2$O | m-xylene | NaBH$_4$ | 87 | 6 |
| 24[a,g,i,n] | Pd(OH)$_2$/C | NH$_3$ · H$_2$O | m-xylene | NaBH$_4$ | 88 | 6 |
| 25[d,g,i,n] | Pd(OH)$_2$/C | NH$_3$ · H$_2$O | m-xylene | NaBH$_4$ | 68 | 5 |

[a]General conditions: 1a (0.2 mmol), 2a (3 equiv), catalyst (20 mol %), HCO$_2$Na (3 equiv), and solvent (1 mL) at 160 °C. for 24 h under an argon atmosphere.
[b]Yields were determined by $^1$H NMR with nitromethane as internal standard, isolated yields in brackets.
[c]NH$_3$ · H$_2$O (2 equiv).
[d]NH$_3$ · H2O (5 equiv).
[e]NH$_3$ · H2O (6 equiv).
[f]NaBH$_4$ (1.5 equiv).
[g]NaBH$_4$ (1 equiv).
[h]NaBH$_4$ (0.5 equiv).
[i]150° C.
[j]140° C.
[k]Pd(OH)$_2$/C (10 mol %).
[l]Pd(OH)$_2$/C (30 mol %).
[m]36 h.
[n]12 h.

Fortunately, a trace amount (ca 2% yield) of N-cyclohexylaniline was detected by ¹H NMR when Pd(OH)₂/C was used as a catalyst in toluene at 160° C. under an argon atmosphere for 24 h using sodium formate as a hydride source (Table 1, entry 1). Other palladium catalysts were also examined without success (Table 1, entries 2-4). Different solvents were then examined (Table 1, entries 5-6), and 6% yield of N-cyclohexylaniline was obtained when m-xylene was used as solvent (Table 1, entry 5). Encouraged by this result, different nitrogen sources such as urea, ammonium bicarbonate, ammonia, hydrazine hydrate and ammonia gas were investigated (Table 1, entries 7-11), with ammonia providing the highest yield (Table 1, entry 9). Adjusting the amount of ammonia to 5 equiv gave the optimal yield (Table 1, entry 13). Increasing or reducing the amount of ammonia led to lower yields (Table 1, entries 12 and 14). Using sodium borohydride, a strong reducing reagent, as hydride source, resulted in 49% yield of N-cyclohexylaniline together with 2% yield of diphenylamine (Table 1, entry 15). Using sodium hydride as the hydride source, a lower yield was observed (Table 1, entry 16). One equiv of NaBH₄ appeared to be optimal for this reaction (Table 1, entry 18), as either higher or lower amounts of NaBH₄ resulted in lower yields (Table 1, entries 17-19). Reducing the reaction temperature to 150° C. gave 87% yield of the product (Table 1, entry 20). Further reducing the temperature lowered the product yield (Table 1, entry 21). The amount of catalyst is also important for the reaction: a lower yield (64%) was achieved when 10 mol % catalyst was used in this reaction system (Table 1, entry 22), and further increasing the amount of catalyst to 30 mol % did not improve the yield (87%) (Table 1, entry 23). Thus, 20 mol % Pd(OH)₂/C was selected as the optimal amount for subsequent optimizations. Nearly the same yield (88%) was obtained when prolonging the reaction time to 36 h (Table 1, entry 24). Reducing the reaction time to 12 h lowered the product yield (Table 1, entry 25). Different phosphine ligands (40 mol %) were tested, including triphenylphosphine, bis(diphenylphosphino)ethane, 1,3-bis(diphenylphosphino)-propane and 1,4-bis(diphenylphosphino)butane, under the standard reaction conditions. These phosphine ligands could not improve the yield, and only recovered the starting material. It is thus provided that Pd(OH)₂/C is reduced by NaBH₄ to form Pd nanoparticles at 150° C. in the proposed catalytic system.

With the optimal reaction conditions established, different symmetrical diaryl ethers were explored to react with 5.0 equiv of ammonia at 150° C. under argon using 20 mol % of Pd(OH)₂/C as the catalyst and 1.0 equiv of sodium borohydride in m-xylene (1 mL) for 24 h. As shown in Table 2, moderate to excellent yields were obtained for various substrates (Table 2, entries 1-7).

TABLE 2

Direct Cross-Coupling of Symmetrical Diaryl Ethers with Ammonia[a]

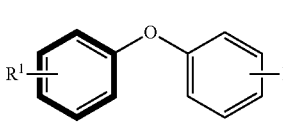

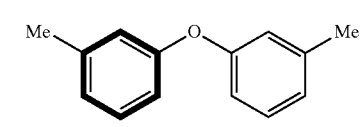

TABLE 2-continued

Direct Cross-Coupling of Symmetrical Diaryl Ethers with Ammonia[a]

$R^1$—[Ar]—O—[Ar]—$R^1$  →  $NH_3 \cdot H_2O$ (5 equiv), $Pd(OH)_2/C$ (20 mol %), $NaBH_4$ (1 equiv), m-xylene (1 mL), 150° C., 24 h, Ar  →  $R^1$—[Ar]—NH—[Cy]—$R^1$  +  [Ar]—$R^1$

1 → 3 + 5

| Entry | Substrates | Products | | |
|---|---|---|---|---|
| 3 | 1c (4-Me-C6H4-O-C6H4-4-Me) | 3c  82%  cis/trans[b] = 19:63 | + | 5b  88%[d] |
| 4 | 1d (4-Et-C6H4-O-C6H4-4-Et) | 3d  69%  cis/trans[b] = 20:49 | + | 5c  80%[d] |
| 5 | 1e (4-nPr-C6H4-O-C6H4-4-nPr) | 3e  71%  cis/trans[b] = 17:54 | + | 5d  83% |
| 6 | 1f (4-F-C6H4-O-C6H4-4-F) | 3a  48%[e] | + | 5a  62%[c] |

TABLE 2-continued

Direct Cross-Coupling of Symmetrical Diaryl Ethers with Ammonia[a]

| Entry | Substrates | Products |
|---|---|---|
| 7 | 1g (MeO—C6H4—O—C6H4—OMe) | 3a (42%[f]) + 5e (58%[c]) |

[a]Reaction conditions: diaryl ether 1 (0.2 mmol), ammonia (1.0 mmol), Pd(OH)$_2$/C (20 mol %), and NaBH$_4$ (0.2 mmol) in m-xylene (1 mL). All reactions were carried out at 150° C. in a sealed tube under an argon atmosphere for 24 h; yields of isolated products were given.
[b]Cis/trans (isomer) ratio was determined by crude $^1$H NMR.
[c]Yields of benzene and cyclohexane was determined by GC-MS; a small peak of cyclohexane was overlapped within the big peak of benzene.
[d]Yield was determined by GC-MS; no corresponding substituted cyclohexane was detected.
eReaction time was prolonged to 36 h, and NaBH$_4$ was increased to 2 equiv.
[f]Reaction time was prolonged to 36 h.

Diphenyl ether was transformed into N-cyclohexylaniline in 83% yield, with the other phenyl group being converted into benzene (82%) as well as a small amount of cyclohexane (Table 2, entry 1). Weakly electron-donating methyl group at meta- and para-positions gave the corresponding anilines 3b and 3c in high yields (Table 2, entries 2-3). Similar results were obtained with longer chain analogs substituted at the para-position (Table 2, entries 4-5). The defluorination product 3a was obtained with moderate yield (48%) when fluorine-containing substrate 1f was explored under the standard conditions with prolonging the reaction time to 36 h and increasing the amount of NaBH$_4$ to 2 equiv (Table 2, entry 6). The 4,4'-dimethoxydiphenyl ether also reacted smoothly, to give the demethoxylation product 3a (Table 2, entry 7).

Subsequently, a wide range of unsymmetrical diaryl ethers were tested. Highly regioselective cleavage of C—O bond was obtained even with only a minute difference between the two aryl groups (Table 3, entries 1-2).

TABLE 3
Direct cross-coupling of unsymmetrical diaryl ethers with ammonia[a]
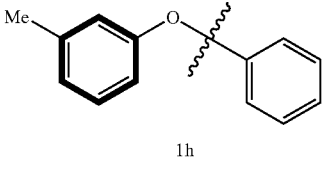
| Entry | Substrates | Products | |
|---|---|---|---|
| 1 | 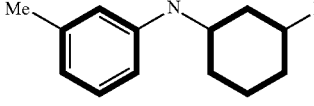 1h | 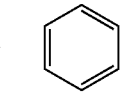 74% cis/trans[b] = 18:56 3a | 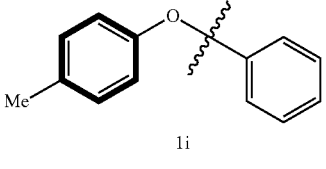 82%[c] 5a |
| 2 | 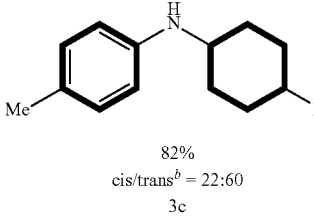 1i | 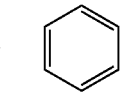 82% cis/trans[b] = 22:60 3c | 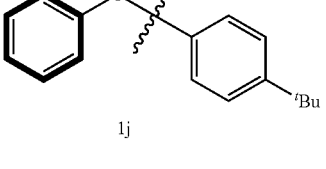 73%[d] 5a |
| 3 | 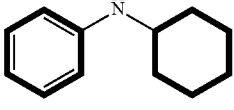 1j | 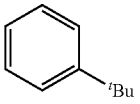 72% 3a | 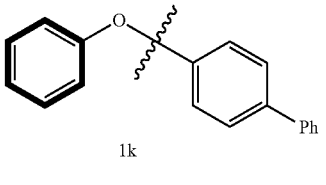 78%[e] 5f |
| 4 | 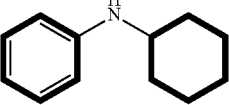 1k | 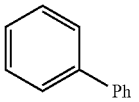 76% 3a | 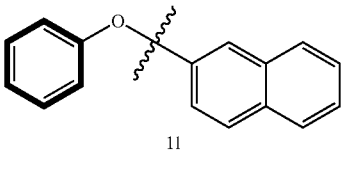 11%[f] 5g |
| 5 | 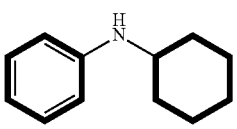 1l | 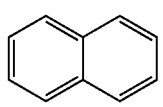 73% 3a | 17%[g] 5h |

TABLE 3-continued

Direct cross-coupling of unsymmetrical diaryl ethers with ammonia[a]

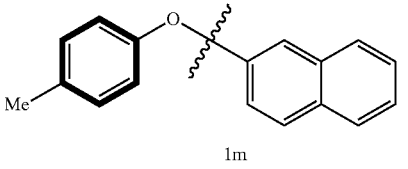

| Entry | Substrates | Products |
|---|---|---|
| 6 | only 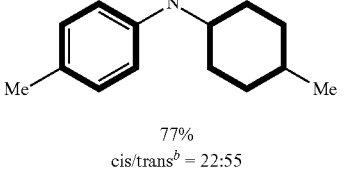 1m | 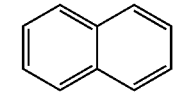 77% cis/trans[b] = 22:55 3c  +  14%[h] 5h |
| 7 | only 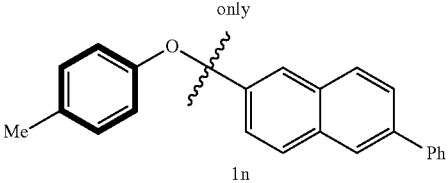 1n | 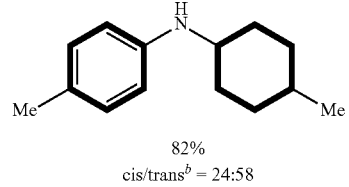 82% cis/trans[b] = 24:58 3c  +  11%[i] 5g |

[a]Reaction conditions: diaryl ether 1 (0.2 mmol), ammonia (1.0 mmol), Pd(OH)$_2$/C (20 mol %), and NaBH$_4$ (0.2 mmol) in m-xylene (1 mL). All reactions were carried out at 150° C. in a sealed tube under an argon atmosphere for 24 h; yields of isolated products were given.
[b]Cis/trans (isomer) ratio was determined by crude $^1$H NMR.
[c]A trace amount of N-cyclohexylaniline and 8% of toluene were also obtained.
[d]A trace amount of N-cyclohexylaniline and 9% of toluene were also obtained.
[e]Isolated yield.
[f]Isolated yield; 82% of cyclohexylbenzene was also obtained.
[g]Isolated yield; in addition, 74% of 1,2,3,4-tetrahydronaphthalene was obtained.
[h]Isolated yield; in addition, 76% of 1,2,3,4-tetrahydronaphthalene was obtained.
[i]Isolated yield; in addition, 81% of cyclohexylbenzene was obtained.

Thus, 3- and 4-methyldiphenyl ethers (1h) and (1i) gave the corresponding methyl substituted cyclohexylaniline 3b and 3c with good to high yields, respectively. The other aryl group of the ethers was converted into the corresponding benzene (65% and 73% yield, respectively) (Table 3, entries 1-2). It is interesting to note that the selectivity of C—O bond cleavage was reversed when the substituent was changed to tert-butyl or phenyl group: cyclohexylaniline (3a) was obtained selectively in high yields, with the other aryl group forming the corresponding arena product tert-butyl benzene (5f) and biphenyl (5g) (Table 3, entries 3-4). It is possible that the solubility might have reversed the selectivity under heterogeneous conditions. 2-Phenoxynaphthalene (1l) and 2-(p-tolyloxy)naphthalene (1m) were also successfully cleaved regioselectively, to give the corresponding cyclohexylaniline (3a) and 4-methyl-N-(4-methylcyclohexyl)aniline (3c) in high yields (Table 3, entries 5-6). When methyl and phenyl group were substituted on both phenyl rings, the regioselective cleavage of C—O bond was achieved (Table 3, entry 7) to give 4-methyl-N-(4-methylcyclohexyl)-aniline (3c) as a single nitrogen-containing product in high yield, together with 11% yield of biphenyl and 81% yield of its reduced product, cyclohexylbenzene.

Figure 2A:
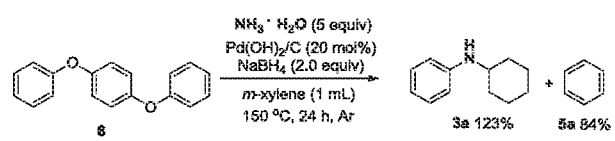
FIG. 2A illustrates schematics conversion of oligomeric phenylene oxides and ammonia into anilines in accordance to an embodiment.
Figure 2B:
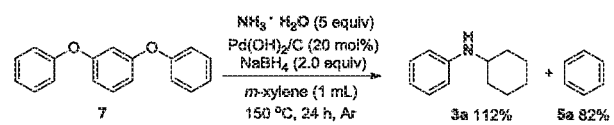
FIG. 2B illustrates schematics conversion of oligomeric phenylene oxides and ammonia into anilines in accordance to another embodiment.

To further investigate the applicability of the catalytic system provided herein, oligomeric phenylene oxides 6 and 7, both containing four C(Ar)—O bonds as polyphenylene oxide (PPO) model compounds, were tested under the standard reaction conditions with increasing sodium borohydride to 2.0 equiv. N-Cyclohexylaniline (3a) and benzene (5a) were obtained with high total yields (123% and 112%, respectively) (FIGS. 2A and 2B), which provide potentials for the valorization of polyphenylene oxide (PPO) wastes.

Figure 3A:
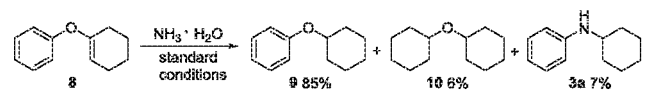
FIG. 3A illustrates control experiments with cyclohexenylphenyl ether in phenol according to an embodiment.
Figure 3B:
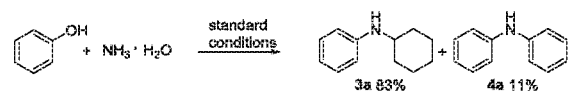
FIG. 3B illustrates control experiments with cyclohexenylphenyl ether in cyclohexanone according to an embodiment.
Figure 3C:
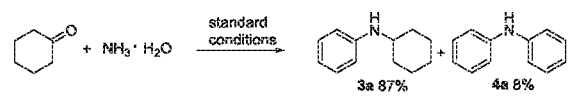
FIG. 3C illustrates control experiments with cyclohexenylphenyl ether reacted with ammonia according to an embodiment.
Figure 4:
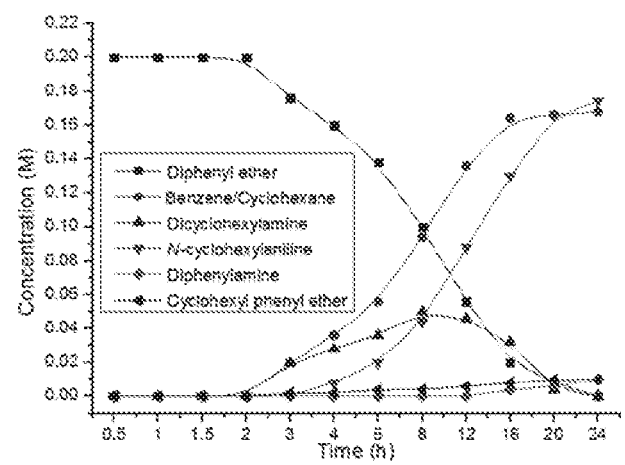
FIG. 4 illustrates a graph showing the concentration of starting material and products at different reaction time.

To understand the reaction mechanism, control experiments were carried out, Cyclohexenylphenyl ether (8) was explored as a possible intermediate under the catalytic system; however, it proved otherwise (FIG. 3A). When diphenyl ether was explored under standard reaction conditions in absence of ammonia, oxygen-containing compounds (phenol and cyclohexanone) and hydrocarbon compounds (benzene and cyclohexane) were obtained. These results illustrated that the C—O bond was directly cleaved via palladium-catalyzed hydrogenolysis of diphenyl ether, which is also consistent with the observation that the nitrogen-containing products (N-cyclohexylaniline, N-dicyclohexylamine and diphenylamine) and hydrocarbon products (benzene and cyclohexane) were formed in ca. 1:1 ratio (FIG. 4), On the other hand, both phenol and cyclohexanone successfully reacted with ammonia (FIGS. 3B and 3c), suggesting their possible involvement as the intermediates in our catalytic system.

Figure 5:
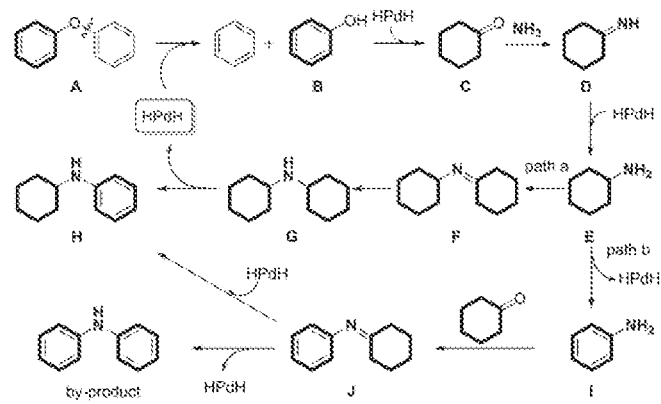
FIG. 5 illustrates a mechanism of amination of diaryl ether as encompassed herein.

Combining these experimental results, a mechanism for this amination reaction is proposed in FIG. 5. The HPd$^{//}$H species is formed by Pd(OH)$_2$/C with sodium borohydride and water. Then, direct cleavage of the C(Ar)—O ether bond by the HPd$^{//}$H via hydrogenolysis of diphenyl ether generates benzene and phenol B, which is further reduced by HPd$^{//}$H to form cyclohexanone C.[10] Then, C condenses with ammonia to form imine D, which is further reduced to form amine E. Condensation of E with cyclohexanone generates imine F (path a), which is reduced to dicyclohexylamine G. Amine G then oxidatively aromatizes to form the product N-cyclohexylaniline H, as well as regenerates HPd$^{//}$H. Alternatively, amine E undergoes oxidative aromatization to generate aniline I (path b),[11] which is condensed with cyclohexanone to form imine J. Intermediate J is reduced to generate the product H and a small amount of J is oxidized to form by-product diphenylamine.

It is thus provided a palladium-catalyzed synthesis of aniline derivatives from 4-O-5 linkage lignin model compounds and cheap industrial inorganic chemical ammonia via dual C(Ar)—O bond cleavage. Various symmetrical and unsymmetrical diaryl ethers reacted with ammonia to form the corresponding aniline derivatives and arene products. Furthermore, the method can also be extended to oligomeric phenylene oxide, which provides potential for the valorization of polyphenylene oxide (PPO) wastes.

While the present disclosure has been described in connection with specific embodiments thereof, it will be understood that it is capable of further modifications and this application is intended to cover any variations, uses, or adaptations, including such departures from the present disclosure as come within known or customary practice within the art and as may be applied to the essential features hereinbefore set forth, and as follows in the scope of the appended claims.

What is claimed is:

1. A method of converting a diaryl ether source containing 4-O-5 linkages and an inorganic amine chemical or ammonia into an organic compound, comprising reacting said diaryl ether source with the inorganic amine chemical or the ammonia in presence of a catalyst and a reducing agent, transforming the 4-O-5 linkages of said diaryl ether source into the organic compounds, wherein the reducing agent is HCO$_2$Na, formic acid, ammonium formate, NaH, H$_2$ or NaBH$_4$.

2. The method of claim 1, wherein the diaryl ether source is lignin, polyphenylene oxide (PPO), or a substituted diaryl ether.

3. The method of claim 2, wherein the substituted diaryl ether is substituted with the same or different substituents on the arenes, wherein the substituents are hydrogen, alkyl, halogen, alkoxyl, aryloxy, ester, hydroxyl, amine, nitro, aryl or acyl groups.

4. The method of claim 1, wherein the inorganic amine chemical is ammonium bicarbonate, ammonium chloride, hydrazine hydrate or ammonium hydroxide.

5. The method of claim 1, wherein the catalyst is palladium.

6. The method of claim 1, wherein the catalyst is Pd(OH)$_2$/C.

7. The method of claim 1, wherein the organic compound is at least one of an aniline derivative and an arene.

8. The method of claim 1, further comprising reacting said diaryl ether source, the inorganic amine chemical or the ammonia and the catalyst with a solvent.

9. The method of claim 8, wherein the solvent is m-xylene, o-xylene, p-xylene, toluene or 1,4-dioxane.

10. The method of claim 1, wherein said diaryl ether source is reacted with 5 equiv of ammonia.

11. The method of claim 1, wherein the reducing agent is 1 equiv of NaBH$_4$.

12. The method of claim 1, wherein diaryl ether source, the inorganic amine chemical or the ammonia and the catalyst are contacted at a temperature between 140° C. to 160° C.

13. The method of claim 1, wherein the diaryl ether source and the inorganic amine chemical or the ammonia are contacted with 10 mol % to 30 mol % of the catalyst.

14. The method of claim 1, wherein the said diaryl ether source, the inorganic amine chemical or the ammonia and the catalyst are reacted for 12 to 36 h.

15. The method of claim 1, wherein the inorganic chemical is liquid ammonia or ammonia gas.

* * * * *